United States Patent
Coles et al.

(10) Patent No.: US 9,867,370 B2
(45) Date of Patent: Jan. 16, 2018

(54) COMPOSITIONS AND METHODS FOR STABILIZING CYCLOPROPENE IN SOLUTIONS

(71) Applicant: AgroFresh Inc., Collegeville, PA (US)

(72) Inventors: Jeffrey Alan Coles, Brown Mills, NJ (US); Yueqian Zhen, Paoli, PA (US)

(73) Assignee: AGROFRESH INC., Collegeville, PA (US)

( * ) Notice: Subject to any disclaimer, the term of this patent is extended or adjusted under 35 U.S.C. 154(b) by 0 days.

(21) Appl. No.: 14/760,815

(22) PCT Filed: Jan. 14, 2014

(86) PCT No.: PCT/US2014/011447
§ 371 (c)(1),
(2) Date: Oct. 30, 2015

(87) PCT Pub. No.: WO2014/113375
PCT Pub. Date: Jul. 24, 2014

(65) Prior Publication Data
US 2016/0000072 A1 Jan. 7, 2016

Related U.S. Application Data

(60) Provisional application No. 61/752,611, filed on Jan. 15, 2013.

(51) Int. Cl.
| | | |
|---|---|---|
| *A61K 9/14* | (2006.01) | |
| *A61K 9/48* | (2006.01) | |
| *A01N 27/00* | (2006.01) | |
| *A01N 3/02* | (2006.01) | |
| *A01N 25/02* | (2006.01) | |
| *A01N 25/22* | (2006.01) | |
| *A01N 43/16* | (2006.01) | |
| *A23B 7/154* | (2006.01) | |

(52) U.S. Cl.
CPC ............... *A01N 27/00* (2013.01); *A01N 3/02* (2013.01); *A01N 25/02* (2013.01); *A01N 25/22* (2013.01); *A01N 43/16* (2013.01); *A23B 7/154* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,879,188 A | 4/1975 | Fritz |
| 5,518,988 A | 5/1996 | Sisler |
| 6,017,849 A | 1/2000 | Daly |
| 6,313,068 B1 | 11/2001 | Daly |
| 2005/0288189 A1 | 12/2005 | Jacobson |

FOREIGN PATENT DOCUMENTS

| | | | |
|---|---|---|---|
| EP | 1192859 | * | 4/2002 |
| EP | 1304035 | * | 4/2003 |
| EP | 2283727 | * | 8/2009 |
| EP | 2283727 | | 2/2011 |
| EP | 2389814 | | 11/2011 |
| WO | WO2008/071714 | | 6/2008 |

OTHER PUBLICATIONS

Roberts D D et al: Effects of Sucrose, Guar Gum, and Carboxymethycellulose on the Release of Volatile Flavor Compounds Under Dynamic Conditions, Journal of Agricultural and Food Chemistry, American Chemical Society, US vol. 44, No. 5, May 1, 1996.
Nahon, Denise F., et al. "Flavor release from mixtures of sodium cyclamate, sucrose, and an orange aroma." Journal of Agricultural and Food Chemistry 46.12 (1998): 4963-4968.
International Search Report PCT/US2014/011447 date mailed Jul. 31, 2014 pp. 1-4.

* cited by examiner

*Primary Examiner* — Alton Pryor
(74) *Attorney, Agent, or Firm* — Barnes & Thornburg LLP

(57) ABSTRACT

This invention is based on surprising results that certain concentrations of certain sugars stabilize cyclopropene formulation in aqueous solutions. Provided are compositions comprising an aqueous solution of at least one cyclopropene and at least one sugar. Also provided are methods of using such compositions for inhibiting an ethylene response in a plant.

18 Claims, 1 Drawing Sheet

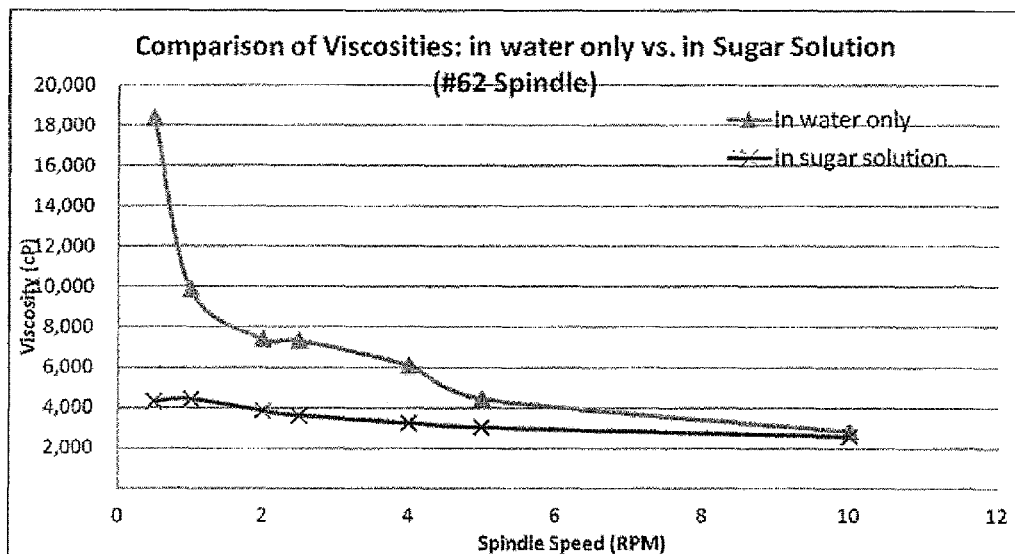

COMPOSITIONS AND METHODS FOR STABILIZING CYCLOPROPENE IN SOLUTIONS

BACKGROUND OF THE INVENTION

For the use of cyclopropenes, the cyclopropene is often in the form of a complex with a molecular encapsulating agent. Such a complex is useful, for example, for use in treating plants or plant parts by contacting the plants or plant parts with the complex in order to bring about contact between the plants or plant parts and the cyclopropene. Such treatment of plants or plant parts is often effective at desirably interrupting one or more ethylene-mediated process in the plants or plant parts. For example, such treatment of plant parts can sometimes desirably delay unwanted ripening. For another example, such treatment of crop plants prior to harvest can sometimes improve the yield of the crop.

U.S. Pat. No. 6,313,068 discloses grinding and milling of dried powder of a complex of cyclodextrin and methylcyclopropene.

It is often useful to dissolve or suspend particles of such a complex in a liquid. However, when the liquid is an aqueous solution, it is sometimes found that contact between the water and the particles of the complex causes release of cyclopropene from the complex earlier than desired, and some or all of the cyclopropene is thus lost to the surroundings or destroyed by a chemical reaction or a combination thereof. Therefore, it is often desirable to suspend such particles in oil. However, in the past, attempts to suspend such particles in oil have found that such particles could not be suspended effectively in oil, often because the suspensions could not be sprayed properly, or because the suspensions had too high viscosity at reasonable concentration of particles, or because the suspensions were not stable, or because the suspensions had some combination of these problems.

Thus, there remains a need for stable liquid formulation for cyclopropene.

SUMMARY OF THE INVENTION

This invention is based on surprising results that certain concentrations of certain sugars may stabilize cyclopropene formulation in aqueous solutions. Provided are compositions comprising an aqueous solution of at least one cyclopropene and at least one sugar. Also provided are methods of using such compositions for inhibiting an ethylene response in a plant.

In one aspect, provided is a composition comprising an aqueous solution of a cyclopropene and at least one sugar.

In one embodiment, the cyclopropene is part of a cyclopropene molecular complex. In another embodiment, the cyclopropene molecular complex is an inclusion complex. In another embodiment, the cyclopropene molecular complex comprises a cyclopropene and a molecular encapsulating agent. In a further embodiment, the molecular encapsulating agent is selected from the group consisting of substituted cyclodextrins, unsubstituted cyclodextrins, crown ethers, zeolites, and combinations thereof. In a further embodiment, the molecular encapsulating agent comprises a cyclodextrin. In another embodiment, the molecular encapsulating agent is selected from the group consisting of alpha-cyclodextrin, beta-cyclodextrin, gamma-cyclodextrin, and combinations thereof. In a further embodiment, the molecular encapsulating agent comprises alpha-cyclodextrin.

In one embodiment, the compositions comprises from 0.1 to 10 percent (w/w) of a cyclopropene. In another embodiment, the compositions comprises from 0.3 to 3 percent (w/w) of a cyclopropene. In some embodiments, the composition may comprise 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, or 10 percent (w/w) of a cyclopropene. In another embodiment, the composition comprises at least 0.1 or 1 percent (w/w) of a cyclopropene.

In one embodiment, the aqueous solution is at least 25% saturated with the at least one sugar. In another embodiment, the aqueous solution is 25-35%, 25-50%, or 35-60% saturated with the at least one sugar. In another embodiment, the aqueous solution is 90-100% saturated with sucrose. In another embodiment, the at least one sugar is selected from the group consisting of monosaccharides, disaccharides, and combinations thereof. In another embodiment, the at least one sugar comprises sucrose.

In one embodiment, the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In one embodiment, the cyclopropene is of the formula:

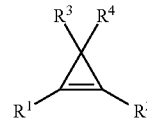

wherein $R^1$ is a substituted or unsubstituted $C_1$-$C_4$ alkyl, $C_1$-$C_4$ alkenyl, alkynyl, $C_1$-$C_4$ cylcoalkyl, cylcoalkylalkyl, phenyl, or napthyl group; and $R^2$, $R^3$, and $R^4$ are hydrogen.

In a further embodiment, the cyclopropene is 1-methylcyclopropene (1-MCP).

In one embodiment, the cyclopropene content of the composition is stable over a period of at least ten (10), twenty (20), thirty (30), or sixty (60) days. In another embodiment, the cyclopropene content of the composition is stable over a period of one month, two months, three months, six months, or twelve months. In another embodiment, the cyclopropene content of the composition is stable over a period of one year, two years, or three years.

In another aspect, provided is a composition comprising (a) an aqueous solution of at least one cyclopropene molecular complex comprising a cyclopropene and a molecular encapsulating agent selected from the group consisting of substituted cyclodextrins, unsubstituted cyclodextrins, crown ethers, zeolites, and combinations thereof; and (b) at least one sugar selected from the group consisting of monosaccharides, disaccharides, trisaccharides, oligosaccharides, polysaccharides, and combinations thereof.

In another aspect, provided is a method of inhibiting an ethylene response in a plant, the method comprising treating the plant with the composition provided herein. In one embodiment of the methods provided, the cyclopropene is part of a cyclopropene molecular complex. In another embodiment, the cyclopropene molecular complex is an inclusion complex. In another embodiment, the cyclopropene molecular complex comprises a cyclopropene and a molecular encapsulating agent. In a further embodiment, the molecular encapsulating agent is selected from the group consisting of substituted cyclodextrins, unsubstituted cyclodextrins, crown ethers, zeolites, and combinations thereof. In a further embodiment, the molecular encapsulating agent comprises a cyclodextrin. In another embodiment, the molecular encapsulating agent is selected from the group consisting of alpha-cyclodextrin, beta-cyclodextrin, gamma-cyclodextrin, and combinations thereof. In a further embodiment, the molecular encapsulating agent comprises alpha-cyclodextrin.

In one embodiment of the methods provided, the aqueous solution is at least 25% saturated with the at least one sugar. In another embodiment, the aqueous solution is 25-35%, 25-50%, or 35-60% saturated with the at least one sugar. In another embodiment, the aqueous solution is 90-100% saturated with sucrose. In another embodiment, the at least one sugar is selected from the group consisting of monosaccarides, disaccharides, and combinations thereof. In another embodiment, the at least one sugar comprises sucrose.

In one embodiment of the methods provided, the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In one embodiment, the cyclopropene is of the formula:

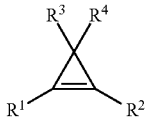

wherein $R^1$ is a substituted or unsubstituted $C_1$-$C_4$ alkyl, $C_1$-$C_4$ alkenyl, $C_1$-$C_4$ alkynyl, $C_1$-$C_4$ cylcoalkyl, cylcoalkylalkyl, phenyl, or napthyl group; and $R^2$, $R^3$, and $R^4$ are hydrogen.

In a further embodiment, the cyclopropene is 1-methylcyclopropene (1-MCP).

In one embodiment, the cyclopropene content of the composition is stable over a period of at least ten (10); twenty (20), thirty (30), or sixty (60) days. In another embodiment, the cyclopropene content of the composition is stable over a period of one month, two months, three months, six months, or twelve months. In another embodiment, the cyclopropene content of the composition is stable over a period of one year, two years, or three years.

BRIEF DESCRIPTION OF THE DRAWINGS

FIG. 1 shows a representative comparison of viscosities between formulations with or without sugar.

DETAILED DESCRIPTION OF THE INVENTION

As used herein, a cyclopropene is any compound with the formula

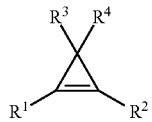

where each $R^1$, $R^2$, $R^3$ and $R^4$ is independently selected from the group consisting of H and a chemical group of the formula:

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, but are not limited to, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent. It is contemplated that such substituted groups may be made by any method, including but not limited to making the unsubstituted form of the chemical group of interest and then performing a substitution. Suitable substituents include, but are not limited to, alkyl, alkenyl, acetylamino, alkoxy, alkoxyalkoxy, alkoxycarbonyl, alkoxyimio, carboxy, halo, haloalkoxy, hydroxy, alkylsulfonyl, alkylthio, trialkylsilyl, dialkylamino, and combinations thereof. An additional suitable substituent, which, if present, may be present alone or in combination with another suitable substituent, is -(L)$_m$-Z where m is 0 to 8, and where L and Z are defined herein above. If more than one substituent is present on a single chemical group of interest, each substituent may replace a different hydrogen atom, or one substituent may be attached to another substituent, which in turn is attached to the chemical group of interest, or a combination thereof.

Among the suitable $R^1$, $R^2$, $R^3$, and $R^4$ groups are, without limitation, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, without limitation, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, without limitation, alkylphosphonato, dialkylphosphato, dialkylthiophosphato, dialkylamino, alkylcarbonyl, and dialkylaminosulfonyl.

Also among the suitable $R^1$, $R^2$, $R^3$, and $R^4$ groups are, without limitation, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, without limitation, substituted and unsubstituted heterocyclyl groups (i.e., aromatic or non-aromatic cyclic groups with at least one heteroatom in the ring).

Also among the suitable $R^1$, $R^2$, $R^3$, and $R^4$ groups are, without limitation, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, without limitation, substituted and unsubstituted aryl groups. Suitable substituents include those described herein above. In some embodiments, one or more substituted aryl group may be used in which at least one substituent is one or more of alkenyl, alkyl, alkynyl, acetylamino, alkoxyalkoxy, alkoxy, alkoxycarbonyl, carbonyl, alkylcarbonyloxy, carboxy, arylamino, haloalkoxy, halo, hydroxy, trialkylsilyl, dialkylamino, alkylsulfonyl, sulfonylalkyl, alkylthio, thioalkyl, arylaminosulfonyl, and haloalkylthio.

Also among the suitable $R^1$, $R^2$, $R^3$, and $R^4$ groups are, without limitation, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, without limitation, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, without limitation, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, without limitation, a substituted or unsubstituted cyclopropane, cyclopropene, epoxide, or aziridine ring.

In some embodiments, G is a ring system that contains a 4 membered heterocyclic ring; in some of such embodiments, the heterocyclic ring contains exactly one heteroatom. In some embodiments, G is a ring system that contains a heterocyclic ring with 5 or more members; in some of such embodiments, the heterocyclic ring contains 1 to 4 heteroatoms. In some embodiments, the ring in G is unsubstituted; in other embodiments, the ring system contains 1 to 5 substituents; In some embodiments in which G contains substituents, each substituent may be independently chosen from the substituents described herein above. Also suitable are embodiments in which G is a carbocyclic ring system.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments are included those embodiments, for example, in which G is unsubstituted or substituted phenyl, cyclopentyl, cycloheptyl, or cyclohexyl. In some embodiments, G is cyclopentyl, cycloheptyl, cyclohexyl, phenyl, or substituted phenyl. Among embodiments in which G is substituted phenyl are embodiments, without limitation, in which there are 1, 2, or 3 substituents. In some embodiments in which G is substituted phenyl are embodiments, without limitation, in which the substituents are independently selected from methyl, methoxy, and halo.

Also contemplated are embodiments in which $R^3$ and $R^4$ are combined into a single group, which may be attached to the number 3 carbon atom of the cyclopropene ring by a double bond. Some of such compounds are described in U.S. Patent Publication 2005/0288189.

In some embodiments, one or more cyclopropenes may be used in which one or more of $R^1$, $R^2$, $R^3$, and $R^4$ is hydrogen. In some embodiments, $R^1$ or $R^2$ or both $R^1$ and $R^2$ may be hydrogen. In some embodiments, $R^3$ or $R^4$ or both $R^3$ and $R^4$ may be hydrogen. In some embodiments, $R^2$, $R^3$, and $R^4$ may be hydrogen.

In some embodiments, one or more of $R^1$, $R^2$, $R^3$, and $R^4$ may be a structure that has no double bond. Independently, In some embodiments, one or more of $R^1$, $R^2$, $R^3$, and $R^4$ may be a structure that has no triple bond. In some embodiments, one or more of $R^1$, $R^2$, $R^3$, and $R^4$ may be a structure that has no halogen atom substituent. In some embodiments, one or more of $R^1$, $R^2$, $R^3$, and $R^4$ may be a structure that has no substituent that is ionic.

In some embodiments, one or more of $R^1$, $R^2$, $R^3$, and $R^4$ may be hydrogen or $(C_1$-$C_{10})$ alkyl. In some embodiments, each of $R^1$, $R^2$, $R^3$, and $R^4$ may be hydrogen or $(C_1$-$C_8)$ alkyl. In some embodiments, each of $R^1$, $R^2$, $R^3$, and $R^4$ may be hydrogen or ($C_1$-$C_4$) alkyl. In some embodiments, each of $R^1$, $R^2$, $R^3$, and $R^4$ may be hydrogen or methyl. In some embodiments, $R^1$ may be ($C_1$-$C_4$) alkyl and each of $R^2$, $R^3$, and $R^4$ may be hydrogen. In some embodiments, $R^1$ may be methyl and each of $R^2$, $R^3$, and $R^4$ may be hydrogen, and the cyclopropene is known herein as "1-MCP."

In some embodiments, a cyclopropene may be used that has boiling point at one atmosphere pressure of 50° C. or lower; or 25° C. or lower; or 15° C. or lower. In some embodiments, a cyclopropene may be used that has boiling point at one atmosphere pressure of −100° C. or higher; −50° C. or higher; or −25° C. or higher; or 0° C. or higher.

The cyclopropenes may be prepared by any method. Some suitable methods of preparation of cyclopropenes include, but are not limited to, the processes disclosed in U.S. Pat. Nos. 5,518,988 and 6,017,849.

In some embodiments, the composition may include at least one molecular encapsulating agent for the cyclopropene. In some embodiments, at least one molecular encapsulating agent may encapsulate one or more cyclopropene or a portion of one or more cyclopropene. A complex that contains a cyclopropene molecule or a portion of a cyclopropene molecule encapsulated in a molecule of a molecular encapsulating agent is known herein as a "cyclopropene molecular complex" or "cyclopropene compound complex." In some embodiments, cyclopropene molecular complexes may comprise at least 1, 2, 3, 4, 5, 6, 7, 8, 9, 10, 20, 30, 32, 40, 50, 60, 70, 80, or 90% (w/w) of the solution.

In some embodiments, at least one cyclopropene molecular complex may be present as an inclusion complex. In such an inclusion complex, the molecular encapsulating agent forms a cavity, and the cyclopropene or a portion of the cyclopropene is located within that cavity. In some embodiments of inclusion complexes, there may be no covalent bonding between the cyclopropene and the molecular encapsulating agent. In some embodiments of inclusion complexes, there may be no ionic bonding between the cyclopropene and the molecular encapsulating agent, whether or not there is any electrostatic attraction between one or more polar moiety in the cyclopropene and one or more polar moiety in the molecular encapsulating agent.

In some embodiments of inclusion complexes, the interior of the cavity of the molecular encapsulating agent may be substantially apolar or hydrophobic or both, and the cyclopropene (or the portion of the cyclopropene located within that cavity) is also substantially apolar or hydrophobic or both. While the present invention is not limited to any particular theory or mechanism, it is contemplated that, in such apolar cyclopropene molecular complexes, van der Waals forces, or hydrophobic interactions, or both, cause the cyclopropene molecule or portion thereof to remain within the cavity of the molecular encapsulating agent.

The cyclopropene molecular complexes may be prepared by any means. In one method of preparation, for example, such complexes may be prepared by contacting the cyclopropene with a solution or slurry of the molecular encapsulating agent and then isolating the complex, using, for example, processes disclosed in U.S. Pat. No. 6,017,849. For example, in another method of making a complex in which cyclopropene is encapsulated in a molecular encapsulating agent, the cyclopropene gas may be bubbled through a solution of molecular encapsulating agent in water, from which the complex first precipitates and is then isolated by filtration. In some embodiments, complexes may be made by either of the above methods and, after isolation, may be dried and stored in solid form, for example as a powder, for later addition to useful compositions.

The amount of molecular encapsulating agent may be characterized by the ratio of moles of molecular encapsulating agent to moles of cyclopropene. In some embodiments, the ratio of moles of molecular encapsulating agent to moles of cyclopropene may be 0.1 or larger; 0.2 or larger; 0.5 or larger; or 0.9 or larger. In some embodiments, the ratio of moles of molecular encapsulating agent to moles of cyclopropene may be 2 or lower; or 1.5 or lower.

Suitable molecular encapsulating agents include, without limitation, organic and inorganic molecular encapsulating agents. Suitable organic molecular encapsulating agents include, without limitation, substituted cyclodextrins, unsubstituted cyclodextrins, and crown ethers. Suitable inorganic molecular encapsulating agents include, without limitation, zeolites. Mixtures of suitable molecular encapsulating agents are also suitable. In some embodiments, the encapsulating agent may be alpha-cyclodextrin, beta-cyclodextrin, gamma-cyclodextrin, or a mixture thereof. In some embodiments, alpha-cyclodextrin may be used. In some embodiments, the encapsulating agent may vary depending upon the structure of the cyclopropene or cyclopropenes being used. Any cyclodextrin or mixture of cyclodextrins, cyclodextrin polymers, modified cyclodextrins, or mixtures thereof may also be utilized. Some cyclodextrins are available, for example, from Wacker Biochem Inc., Adrian, Mich. or Cerestar USA, Hammond, Ind., as well as other vendors.

As used herein, the phrase "sugar" refers to any water-soluble crystalline carbohydrates. "Sugar" includes monomer (monosaccharide), dimer (disaccharide), trimer (trisaccharide), multimer (multisaccharide), or polymer (polysaccharide) of pentose (five-member ring sugar) or hexose (six-member ring sugar). Examples of such pentoses or hexoses include glucose, mannose, arabinose, galactose, and fructose. In one embodiment, sugar of the subject invention includes dextrins and maltodextrins, for example Maltrin M040 from Grain Processing Corporation, which are soluble in water up to 40% and includes syrup. In another embodiment, sugar of the subject invention comprises sucrose, which is a disaccharide of glucose and fructose.

In some embodiments the one or more sugars may be any kind of sugar or sugar derivative. In some embodiments, the one or more sugars may be a monosaccharide, a disaccharide, or combinations thereof. Examples of monosaccharides include, but are not limited to, glucoses, galactoses, riboses, and fructoses. Examples of sugar derivatives include, but are not limited to β-D-Glucose, β-D-Glucose 6 phosphate, β-D-Glucosamine, N-Acetyl-β-D-Glucosamine, N-Actylmuramic acid, β-D-Glucoronte, β-D-Gluconate, Galactosamine, Glucosamine, Glucoronate, Gluconate, Sialic acid, Deoxyribose, Fucoses, and Rhamnoses. Examples of disaccharides include, but are not limited to, sucrose, maltose, and lactose.

In some embodiments, the aqueous solution may be at least 10%, 20%, 25%, 30%, 40%, 50%, 60%, 70%, 75%, 80%, 90%, 95%, or 100% saturated with the one or more sugars at standard temperature and pressure. In some embodiments, the aqueous solution may be supersaturated by the one or more sugars. As used herein, "100% saturated" is an aqueous solution wherein the solution can dissolve no more of the one or more sugars at standard temperature and pressure. By way of example, a "50% saturated" solution is an aqueous solution that comprises 50% of the sugar of a 100% saturated solution.

As used herein, the phrase "stable" refer to cyclopropene content at ambient temperature over time, for example after one (1) year, in a solution with no more than 15% loss as compared to day zero (0). When the cyclopropene content is maintained over a period of time, the solution is a "stable" cyclopropene formulation or cyclopropene solution.

In some embodiments, an aqueous solution comprising one or more cyclopropenes and one or more sugars has a more stable cyclopropene content over time than an aqueous solution of one or more cyclopropenes that does not include one or more sugars. In some embodiments, an aqueous solution comprising one or more cyclopropene molecular complexes and one or more sugars has more stable cyclopropene content over time than an aqueous solution of one or more cyclopropene molecular complexes that does not include one or more sugars.

Embodiments include methods of treating plants with the compositions described herein. In some embodiments, treating the plant with the composition inhibits the ethylene response in the plant. The term "plant" is used generically to also include woody-stemmed plants in addition to field crops, potted plants, cut flowers, harvested fruits and vegetables and ornamentals. Examples of plants that can be treated by embodiments include, but are not limited to, those listed below.

In some embodiments, a plant may be treated at levels of cyclopropene that inhibit the ethylene response in the plant. In some embodiments, a plant may be treated at levels that are below phytotoxic levels. The phytotoxic level may vary not only by plant but also by cultivar. Treatment may be performed on growing plants or on plant parts that have been harvested from growing plants. It is contemplated that, in performing the treatment on growing plants, the composition may be contacted with the entire plant or may be contacted with one or more plant parts. Plant parts include any part of a plant, including, but not limited to, flowers, buds, blooms, seeds, cuttings, roots, bulbs, fruits, vegetables, leaves, and combinations thereof. In some embodiments, plants may be treated with compositions described herein prior to or after the harvesting of the useful plant parts.

The compositions described herein may be brought into contact with plants or plant parts by any method, including, for example, spraying, dipping, drenching, fogging, and combinations thereof. In some embodiments, spraying is used.

Suitable treatments may be performed on a plant that is planted in a field, in a garden, in a building (such as, for example, a greenhouse), or in another location. Suitable treatments may be performed on a plant that is planted in open ground, in one or more containers (such as, for example, a pot, planter, or vase), in confined or raised beds, or in other places. In some embodiments, treatment may be performed on a plant that is in a location other than in a building. In some embodiments, a plant may be treated while it is growing in a container such as, for example, a pot, flats, or portable bed.

In some embodiments, the compositions described herein may be diluted prior to the treatment of a plant therewith.

When correctly used, compositions described herein prevent numerous ethylene effects, many of which have been disclosed in U.S. Pat. Nos. 5,518,988 and 3,879,188, both of which are incorporated herein by reference in their entirety. The embodiments described herein may be employed to influence one or more of the plant ethylene responses. Ethylene responses may be initiated by either exogenous or endogenous sources of ethylene. Ethylene responses include, but are not limited to, (i) the ripening and/or senescence of flowers, fruits and vegetables, (ii) the abscission of foliage, flowers and fruit, (iii) the prolongation of the life of ornamentals, such as potted plants, cut flowers, shrubbery and dormant seedlings, (iv) the inhibition of growth in some plants such as the pea plant, and (v) the stimulation of plant growth in some plants such as the rice plant.

Vegetables which may be treated to inhibit senescence include, but are not limited to, leafy green vegetables such as lettuce (e.g., *Lactuea sativa*), spinach (*Spinaca oleracea*) and cabbage (*Brassica oleracea*); various roots such as potatoes (*Solanum tuberosum*), carrots (*Daucus*); bulbs such as onions (*Allium* sp.); herbs such as basil (*Ocimum basilicum*), oregano (*Origanum vulgare*) and dill (*Anethum graveolens*); as well as soybean (*Glycine max*), lima beans (*Phaseolus limensis*), peas (*Lathyrus* sp.), corn (*Zea mays*), broccoli (*Brassica oleracea italica*), cauliflower (*Brassica oleracea botrytis*) and asparagus (*Asparagus officinalis*).

Fruits which may be treated by the methods of the present invention to inhibit ripening include, but are not limited to, tomatoes (*Lycopersicon esculentum*), apples (*Malus domestica*), bananas (*Musa sapientum*), pears (*Pyrus communis*), papaya (*Carica papya*), mangoes (*Mangifera indica*), peaches (*Prunus persica*), apricots (*Prunus armeniaca*), nectarines (*Prunus persica nectarina*), oranges (*Citrus* sp.), lemons (*Citrus limonia*), limes (*Citrus aurantifolia*), grapefruit (*Citrus paradisi*), tangerines (*Citrus nobilis deliciosa*), kiwi (*Actinidia chinenus*), melons such as cantaloupes (*C. cantalupensis*) and musk melons (*C. melo*), pineapples (*Aranae comosus*), persimmon (*Diospyros* sp.) and raspberries (e.g., *Fragaria* or *Rubus ursinus*), blueberries (*Vaccinium* sp.), green beans (*Phaseolus vulgaris*), members of the genus *Cucumis* such as cucumber (*C. sativus*) and avocados (*Persea americana*).

Ornamental plants which may be treated by the methods of the present invention to inhibit senescence and/or to prolong flower life and appearance (such as the delay of wilting), include, but are not limited to, potted ornamentals and cut flowers. Potted ornamentals and cut flowers which may be treated include, but are not limited to, azalea (*Rhododendron* spp.), hydrangea (*Macrophylla hydrangea*), hibiscus (*Hibiscus rosasanensis*), snapdragons (*Antirrhinum* sp.), poinsettia (*Euphorbia pulcherima*), cactus (e.g., *Cactaceae schlumbergera truncata*), begonias (*Begonia* sp.), roses (*Rosa* sp.), tulips (*Tulipa* sp.), daffodils (*Narcissus* sp.), petunias (*Petunia hybrida*), carnation (*Dianthus caryophyllus*), lily (e.g., *Lilium* sp.), gladiolus (*Gladiolus* sp.), Alstroemeria (*Alstroemaria brasiliensis*), anemone (e.g., *Anemone bland*), columbine (*Aquilegia* sp.), aralia (e.g., *Aralia chinesis*), aster (e.g., *Aster carolinianus*), bougainvillea (*Bougainvillea* sp.), camellia (*Camellia* sp.), bellflower (*Campanula* sp.), cockscomb (*Celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

Plants which may be treated to inhibit abscission of foliage, flowers, and fruit include, but are not limited to, cotton (*Gossypium* spp.), apples, pears, cherries (*Prunus avium*), pecans (*Carva illinoensis*), grapes (*Vitis vinifera*), olives (e.g., *Olea europaea*), coffee (*Coffea arabica*), snapbeans (*Phaseolus vulgaris*), and weeping fig (*Ficus benjamina*), as well as dormant seedlings including, but not limited to, those of various fruit trees including apple, ornamental plants, shrubbery, and tree seedlings.

In addition, shrubbery which may be treated to inhibit abscission of foliage include, but are not limited to, privet (*Ligustrum* sp.), photinea (*Photina* sp.), holly (*Ilex* sp.), ferns of the family Polypodiaceae, schefflera (*Schefflera* sp.), aglaonema (*Aglaonema* sp.), cotoneaster (*Cotoneaster* sp.), barberry (*Berberris* sp.), waxmyrtle (*Myrica* sp.), abelia (*Abelia* sp.), acacia (*Acacia* sp.), and bromeliades of the family Bromeliaceae.

In some embodiments, the compositions described herein may be used to treat a plant growing in a field. Such a treatment operation may be performed one time or more than one time on a particular group of crop during a single growing season. In some embodiments, the amount of cyclopropene used in one treatment may be 0.1 gram per hectare (g/ha) or more; or 0.5 g/ha or more; or 1 g/ha or more; or 5 g/ha or more; or 25 g/ha or more; or 50 g/ha or more; or 100 g/ha or more. In some embodiments, the amount of cyclopropene used in one spraying operation may be 6000 g/ha or less; or 3000 g/ha or less; or 1500 g/ha or less.

As used herein, the phrase "plant" includes dicotyledons plants and monocotyledons plants. Examples of dicotyledons plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the phrase "plant material" refers to leaves, stems, roots, flowers or flower parts, fruits, pollen, egg cells, zygotes, seeds, cuttings, cell or tissue cultures, or any other part or product of a plant. In some embodiment, plant material includes cotyledon and leaf.

A used herein, the phrase "plant tissue" refers to a group of plant cells organized into a structural and functional unit. Any tissue of a plant in planta or in culture is included, for example: whole plants, plant organs, plant seeds, tissue culture and any groups of plant cells organized into structural and/or functional units.

In some embodiments, the compositions described herein or diluted solutions derived from may be used to treat a plant growing in a field. Such a treatment operation may be performed two or more times on a particular group of crop during a single growing season. In some embodiments, the amount of cyclopropene used in any single treatment may be 0.1 gram per hectare (g/ha) or more; or 0.5 g/ha or more; or 1 g/ha or more; or 5 g/ha or more; or 10 g/ha or more; or 25 g/ha or more; or 50 g/ha or more; or 100 g/ha or more. In some embodiments, the amount of cyclopropene used in one application may be 6000 g/ha or less; or 3000 g/ha or less; or 1500 g/ha or less; or 1000 g/ha or less; or 500 g/ha or less; or 250 g/ha or less; or 100 g/ha or less; or 50 g/ha or less; or 25 g/ha or less; or 10 g/ha or less; or 5 g/ha or less; or 1 g/ha or less.

It is to be understood that for purposes of the present specification and claims that the range and ratio limits recited herein can be combined. For example, if ranges of 60 to 120 and 80 to 110 are recited for a particular parameter, it is understood that the ranges of 60 to 110 and 80 to 120 are also contemplated. As a further, independent example, if a particular parameter is disclosed to have suitable minima of 1, 2, and 3, and if that parameter is disclosed to have suitable maxima of 9 and 10, then all the following ranges are contemplated: 1 to 9, 1 to 10, 2 to 9, 2 to 10, 3 to 9, and 3 to 10.

The present invention is further described in the following examples, which are offered by way of illustration and are not intended to limit the invention in any manner.

EXAMPLES

Example 1

Sixty-eight grams of HAIP powder (High Active Ingredient Particles; a powder of 1-MCP complexed with cyclodextrin) is added to 144.5 grams of near saturated (66%) sucrose solution. The samples are kept at room temperature and 1-MCP contents are measured after a specified period of time. The amount of 1-MCP in the solution is monitored over time and shown in Table 1.

TABLE 1

Stability analysis

| Day(s) | Average % 1-MCP in sample |
|---|---|
| 0 | 1.17 |
| 39 | 1.12 |
| 56 | 1.19 |
| 109 | 1.16 |
| 266 | 1.09 |
| 366 | 1.14 |
| 475 | 1.14 |
| 731 | 1.10 |
| 913 | 1.09 |
| 1096 | 1.10 |

Example 2

A headspace assay is used to show that presence of sugar can suppress the loss of 1-MCP into the headspace and maintain a more stable and more flowable formulation as compared to a control formulation without sugar. A liquid formulation (with or without sucrose) comprising 1-MCP is used to partially fill a bottle and then the bottle is sealed air-tight. A headspace between the liquid and top cap of the bottle contains 1-MCP escaped from the liquid formulation. As a consequence, the 1-MCP stability in the liquid formulation can be estimated based on the amount of 1-MCP detected in the headspace (the higher concentration of 1-MCP detected in the headspace, the less stable the formulation will be). Methods for detecting 1-MCP are well-known in the art including, for example, gas chromatography (GC).

Sample 2-1 is prepared by first mixing 89.76 grams of sugar with 46.2 grams of water. After the sugar is completely dissolved, 64 grams of HAIP powder is added to the sugar solution. The powder is mixed well in an open container inside a hood; then the content (~193 grams) is transferred into a 250 ml bottle equipped with a mininert for syringe sampling of the headspace without opening the bottle. The headspace is analyzed for 1-MCP concentration using a GC. 1-MCP concentration in the headspace is expressed as parts per million by volume or ppmv in the headspace.

Sample 2-2 is prepared by mixing 136 grams of HAIP powder with 98.3 grams of water in a beaker inside a hood, under the same HAIP powder to water ratio as Sample 2-1. The slurry (~196 g) is then transferred to a similar 250 ml bottle equipped with a mininert for syringe sampling, and the headspace is analyzed for amount of 1-MCP.

Visually, Sample 2-1 is more flowable and more convenient to use than Sample 2-2, which is more viscous and looks like a paste. In addition to the benefit for a lower viscosity for Sample 2-1, the amount of 1-MCP within the headspace of the samples inside the bottles is much lower for the sugar containing sample (Sample 2-1) than the non-sugar containing Sample 2-2 (see also Table 2 below). Lower amount of 1-MCP in the headspace indicates that more 1-MCP is kept inside the complex and the formulation. Thus, the sugar-containing Sample 2-1 is more stable than the sugar-free Sample 2-2.

Sample 2-3 is prepared by first mixing 120 grams of sucrose with 62 grams of water in a beaker. After the sugar is dissolved completely, 62 grams of HAIP powder is then added to the sugar solution. After the powder is mixed well into the solution, the sample is transferred into a 250 ml bottle equipment with a mininert for air tight syringe sampling. The amount of 1-MCP in the headspace is measured after three and half (3.5) hours of shaking on a Thermo Scientific multi-purpose rotator.

Sample 2-4 is prepared by mixing 113 grams of HAIP powder with 113 grams of water in a beaker in the same HAIP to water mass ration as in Sample 2-3. The slurry is mixed well, then transferred to a 250 ml bottle equipment with a mininert for air tight syringe sampling. The amount of 1-MCP in the headspace is monitored after continuous shaking on a Thermo Scientific multi-purpose rotator.

The viscosities of Sample 2-3 and Sample 2-4 are measured using a Brookfield Viscometer Model DV-II+ Pro and the viscosity versus spinning speed using spindle #62 is shown in FIG. 1, where Sample 2-3 (in sugar solution) has a much lower viscosity and is more flowable than Sample 2-4.

Sample 2-5 is prepared by mixing 50.1 grams of HAIP powder with 150.1 grams of water in a 250 ml bottle for a 25% wt/wt concentration of HAIP powder in water. The sample is shaken vigorously to disperse the solid in water, before it is placed on the rotator for continuous mixing. The amount of 1-MCP in the headspace is measured with a GC after at least 1 hour of agitation, and then the bottle is vented for 30 minutes before being sealed again. The headspace is analyzed again subsequently. This procedure is repeated multiple times, where the equilibrium concentrations of 1-MCP in the headspace are obtained.

Sample 2-6 is prepared by mixing 70 grams of HAIP powder with 130 grams of water in a 250 ml bottle to reach a 35% wt/wt concentration of HAIP powder in water. The sample is mixed and 1-MCP is analyzed in the same way as Sample 2-5.

Table 2 shows the equilibrium concentrations of 1-MCP found in the headspace for Samples 2-1 to 2-6, where the presence of dissolved sucrose can suppress the release/loss of 1-MCP while maintaining a more flowable/more convenient formulation.

TABLE 2

| | Amounts of HAIP in liquid formulations and 1-MCP concentration in headspace | | |
|---|---|---|---|
| Sample# | HAIP concentration wt/wt in formulation | Equilibrium 1-MCP concentration above the formulation/ headspace (ppmv) | Flowability |
| Sample 2-1 | 32% | 4,700 | flowable |
| Sample 2-2 | 58% | 13,400 | high viscosity paste |
| Sample 2-3 | 25% | 5,100 | flowable |
| Sample 2-4 | 50% | 14,700 | high viscosity paste |
| Sample 2-5 | 25% | >20,000 | flowable |
| Sample 2-6 | 35% | >15,000 | flowable |

All references, including publications, patents, and patent applications, cited herein are hereby incorporated by reference to the same extent as if each reference is individually and specifically indicated to be incorporated by reference and is set forth in its entirety herein.

While this invention has been described in certain some embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:
1. A stable liquid composition comprising an aqueous solution of a cyclopropene molecular complex and at least one sugar,
wherein the cyclopropene molecular complex comprises a cyclopropene and a molecular encapsulating agent,
wherein the molecular encapsulating agent is selected from the group consisting of substituted cyclodextrins, unsubstituted cyclodextrins, crown ethers, zeolites, and combinations thereof, and
wherein the aqueous solution is at least 25% saturated with the at least one sugar.
2. The stable liquid composition of claim 1, wherein the cyclopropene molecular complex is an inclusion complex.
3. The stable liquid composition of claim 2, wherein the molecular encapsulating agent forms a cavity and the cyclopropene or a portion of the cyclopropene is located within the cavity.
4. The stable liquid composition of claim 1, wherein the molecular encapsulating agent comprises a cyclodextrin.
5. The stable liquid composition of claim 4, wherein the cyclodextrin is selected from the group consisting of alpha-cyclodextrin, beta-cyclodextrin, gamma-cyclodextrin, and combinations thereof.
6. The stable liquid composition of claim 1, wherein the aqueous solution is 90-100% saturated with the at least one sugar.
7. The stable liquid composition of claim 1, wherein the at least one sugar is selected from the group consisting of monosaccharides, disaccharides, and combinations thereof.
8. The stable liquid composition of claim 1, wherein the at least one sugar comprises sucrose.
9. The stable liquid composition of claim 1, wherein the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.
10. The stable liquid composition of claim 9, wherein R is $C_{1-8}$ alkyl.
11. The stable liquid composition of claim 9, wherein R is methyl.
12. The stable liquid composition of claim 1, wherein the cyclopropene is of the formula:

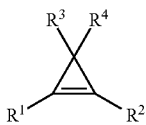

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen.

13. The stable liquid composition of claim 1, wherein the cyclopropene is 1-methylcyclopropene (1-MCP).

14. A method of inhibiting an ethylene response in a plant, the method comprising treating the plant with the stable liquid composition of claim 1.

15. The method of claim 14, wherein the cyclopropene is part of a cyclopropene inclusion complex, the cyclopropene inclusion complex comprising a cyclopropene located in a cavity of the inclusion complex.

16. The method of claim 14, wherein the aqueous solution is 90-100% saturated with the at least one sugar.

17. The method of claim 14, wherein the cyclopropene is 1-methylcyclopropene (1-MCP).

18. A stable liquid composition comprising:
   (a) an aqueous solution of at least one cyclopropene molecular complex comprising a cyclopropene and a molecular encapsulating agent selected from the group consisting of substituted cyclodextrins, unsubstituted cyclodextrins, crown ethers, zeolites, and combinations thereof; and
   (b) at least one sugar selected from the group consisting of monosaccharides, disaccharides, trisaccharides, oligosaccharides, polysaccharides, and combinations thereof,
   wherein the aqueous solution is at least 25% saturated with the at least one sugar.

* * * * *